United States Patent [19]

Young

[11] Patent Number: Plant 5,926

[45] Date of Patent: Apr. 7, 1987

[54] PLUM TREE ("JD-1")

[75] Inventor: John D. Young, Modesto, Calif.

[73] Assignee: Young Family Trust, Modesto, Calif.

[21] Appl. No.: 765,519

[22] Filed: Aug. 14, 1985

[51] Int. Cl.[4] ..... A01H 5/00

[52] U.S. Cl. ..... Plt./38

[58] Field of Search ..... Plt./38

*Primary Examiner*—James R. Feyrer

*Attorney, Agent, or Firm*—Roger B. Webster; William H. Meserole

[57] ABSTRACT

A new and distinct variety of plum tree which is large, vigorous, upright, vase-formed, and hardy; foliated with medium size, ovate, acuminate, acutely pointed leaves having a doubly finely serrate margin, and opposite glands; blooms from hardy, plump, obtuse, free, glabrous flower buds of medium size and length; the flowers being single, blooming early, medium size, and white with a pink tinge; and is a regular and productive bearer of early ripening, uniform, small, broadly ovoid, freestone fruit having vivid, wine red skin with a light bloom, and dark red flesh; the fruit—of fresh market, dessert quality—having a pleasing, desireable flavor.

1 Drawing Figure

BACKGROUND OF THE VARIETY

Field of the Invention

In the maintenance of the garden at my residence, located in Modesto, Stanislaus County, Calif., I frequent such garden for the care of plants and trees growing therein; and against this background of my activities, the present discovery was made by me.

CLASSIFICATION OF THE VARIETY

The present variety of plum tree is embraced by Class 38, Plants, of the U.S. Patent Office Manual of Classification.

PRIOR VARIETIES

Among existing varieties of plum trees which are known to me and mentioned herein, are the ornamental, flowering Blireiana and Hollywood; both believed to be unpatented.

ORIGIN OF THE VARIETY

The original tree of the present variety was purchased by me, from a commercial nursery, under the representation that it was a standard variety of ornamental, flowering plum tree. Subsequent to purchase of the original tree, I planted it in the garden of my residence located as aforesaid. As the tree grew, I maintained it under careful and continued observation and—in maturity—I recognized that the tree evidenced certain characteristics not those of a standard variety of ornamental, flowering plum tree, particularly with respect to the fruit and which was of a size and quality for the fresh fruit market. I, therefore, determined to asexually reproduce the original tree with a view toward ultimate commercialization of the variety.

ASEXUAL REPRODUCTION OF THE VARIETY

The present variety of plum tree was asexually reproduced by budding on compatible rootstock; such asexual reproduction having been undertaken, on my behalf, by an experimental grower on a ranch located near Sanger, Fresno County, Calif. In maturity, such asexual reproductions ran true, in all respects, to the original tree.

SUMMARY OF THE VARIETY

The present variety of plum tree is large, vigorous, upright, vase-formed, and hardy; foliated with medium size, ovate, acuminate, acutely pointed leaves having a doubly finely serrate margin, and opposite glands; blooms from hardy, plump, obtuse, free, glabrous flower buds of medium size and length; the flowers being single, blooming early, medium size, and white with a pink tinge; and is a regular and productive bearer of early ripening, uniform, small, broadly ovoid, freestone fruit having vivid, wine red skin with a light bloom, and dark red flesh; the fruit—of fresh market, dessert quality—having a pleasing, desireable flavor.

The present variety of plum tree is further, and more particularly, characterized as follows:

The present variety of plum tree fairly closely resembles the growth habit of the ornamental, flowering Blireiana, with leaves similar in shape, but having doubly finely serrate leaf margins, whereas the leaf margins of the Blireiana are serrulate. Additionally, the leaves of the present variety have a green-bronze upper surface which is more glabrous and shiny than the Blireiana, while the under surface is a deeper bronze-purplish color. The flowers of the present variety are white and single, whereas the flowers of the Blireiana are semi-double and pink to rose color. The fruit of the present variety ripens early, is freestone, broadly ovoid in shape, vivid wine red color, appealing in quality, pleasing in taste, and of sufficient size to be of commercial value, whereas the fruit of the Blireiana is very small, round-globular (cherry-like), and more soft.

The present variety of plum tree is of somewhat less upright growth than the ornamental, flowering Hollywood; has leaves which are ovate with a doubly finely serrate leaf margin, as distinguished from the substantially obovate leaves with serrate margin of the Hollywood; the leaves having a less bronze upper surface and a less purple under surface than the Hollywood; and the freestone fruit of the present variety, while similar in size, color and shape, ripens about ten to fourteen days earlier than the semi-clingstone fruit of the Hollywood.

BRIEF DESCRIPTION OF THE DRAWING

The drawing is an illustration, by photographic reproduction in color, of a twig with leaves, and with separate fruit, one of the latter being cut in half with the stone remaining in one of the halves.

DESCRIPTION OF THE VARIETY

The botanical details of the present new and distinct variety of plum tree—with color definition in common color terms—are as follows:

Tree:
- *Size.*—Large to medium.
- *Vigor.*—Vigorous.
- *Growth.*—Upright.
- *Form.*—Vase-formed.
- *Hardiness.*—Hardy.
- *Production.*—Productive.
- *Bearing.*—Regular bearer.

Trunk:
- *Size.*—Stocky.
- *Texture.*—Medium.

Branches:
- *Size.*—Medium.
- *Texture.*—Medium.
- *Color.*—Brown, glossy.
- *Lenticels.*—Number: Few. Size: Small.

Leaves:
- *Size.*—Medium. Length range — 3¼"-3½". Width range — 1½"-1¾".
- *Form.*—Ovate. Acuminate. Acutely pointed.
- *Thickness.*—Medium.
- *Color.*—Top side — Light to medium green-bronze. Under side — Bronze-purplish.
- *Texture.*—Smooth.
- *Margin.*—Doubly finely serrate.
- *Petiole.*—Medium length. Medium thickness.
- *Glands.*—Average number — 2 per leaf Opposite Small Globose Red Positioned apical on petiole.
- *Stipules.*—Wanting.

Flower buds:
- *Hardiness.*—Hardy.
- *Size.*—Medium.
- *Length.*—Medium.
- *Form.*—Obtuse Plump Free.
- *Pubescence.*—Glabrous.

Flowers:
- *Blooming period.*—Date of full bloom: Feb. 19, 1985. Early, as compared to other varieties.
- *Size.*—Medium.
- *Form.*—Single.
- *Color.*—White with pink tinge.

Fruit:
- *Maturity when described.*—Firm ripe — June 12, 1985.
- *Date of first picking.*—June 12, 1985.
- *Date of last picking.*—June 24, 1985.
- *Size.*—Uniform. Small. Average diameter axially — 1⅝". Average transversely in suture plane — 1⅞".
- *Form.*—Uniform. Symmetrical. Broadly ovoid. Compressed toward suture.
- *Suture.*—An inconspicuous line extending from base to apex.
- *Ventral surface.*—Rounded slightly.
- *Cavity.*—Rounded. Circular. Average depth — 1/16". Average breadth — ⅛".
- *Base.*—Rounded.
- *Apex.*—Short, Rounded.

Skin:
- *Thickness.*—Thin.
- *Texture.*—Medium.
- *Flavor.*—Slight sour aftertaste.
- *Tenacity.*—Tenacious to flesh.
- *Tendency to crack.*—None.
- *Color.*—Wine red.
- *Down.*—Wanting.
- *Bloom.*—Light.

Flesh:
- *Color.*—Dark red.
- *Surface of pit cavity.*—Dark red throughout.
- *Amygdalin.*—Wanting.
- *Juice.*—Moderate, Rich.
- *Texture.*—Medium. Soft. Fine. Melting.
- *Fibers.*—Few, if any.
- *Ripens.*—Evenly.
- *Flavor.*—Mild. Delicate. Pleasing. Desirable.
- *Aroma.*—Wanting.
- *Eating quality.*—Good.

Stone:
- *Type.*—Freestone. Parts from flesh smoothly. Retains short fiber-like threads along ridges.
- *Size.*—Small. Average length — ⅞". Average breadth — ⅝". Average thickness — 5/16".
- *Form.*—Elliptical. Cuneate toward base and apex.
- *Base.*—Oblique.
- *Hilum.*—Narrow.
- *Apex.*—Acute.
- *Sides.*—Equal. Curved on right and left side.
- *Surface.*—Irregularly ridged near base.
- *Ridges.*—Jagged toward base.
- *Pits.*—Angular.
- *Ventral edge.*—Thin, with wing throughout.
- *Dorsal edge.*—Narrow, with shallow, narrow groove throughout.
- *Color.*—Tan.
- *Tendency to split.*—Slight.

Use: Fresh market; dessert; preserves.

Keeping quality: Medium.

Resistance to insects and diseases: Good to medium.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, characterized, in particular, by the regular and productive bearing of small but marketable size, early ripening, freestone fruit having wine red skin and dark red flesh; the fruit being of good eating quality and pleasing flavor.

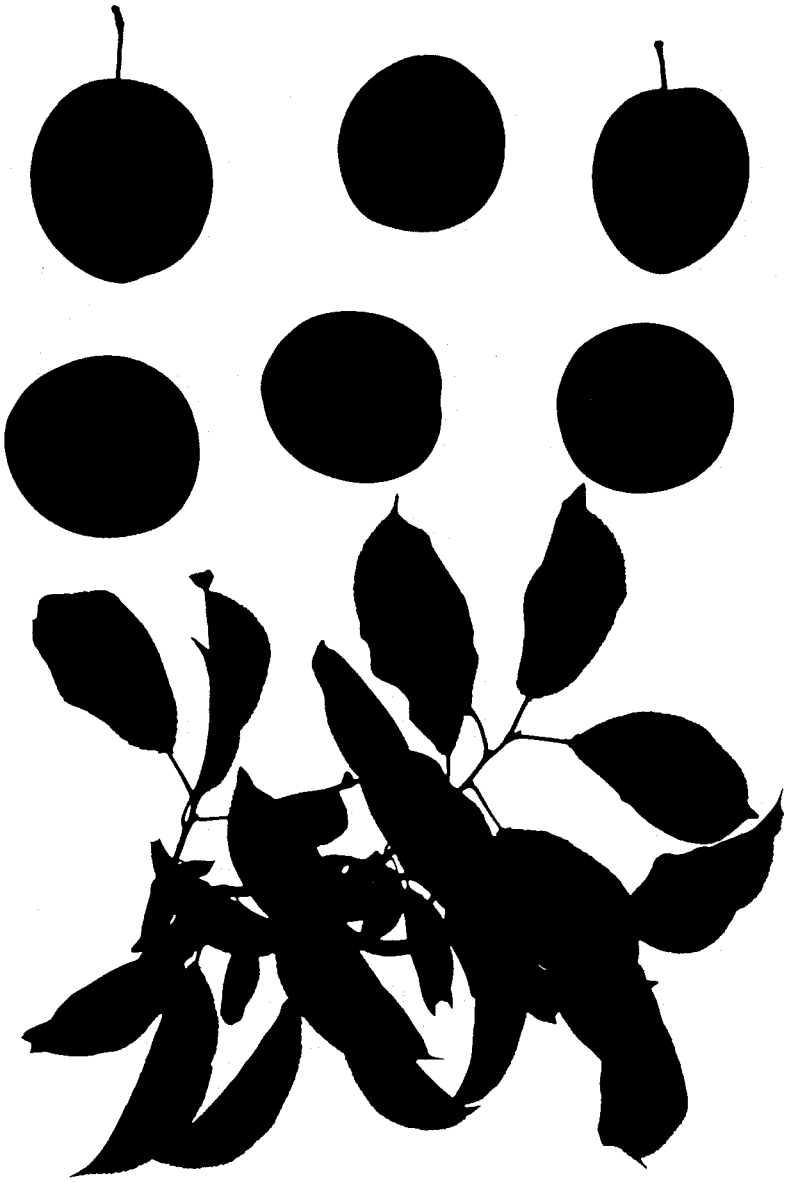

* * * * *